(12) United States Patent
Ng et al.

(10) Patent No.: US 12,361,608 B2
(45) Date of Patent: Jul. 15, 2025

(54) ENHANCEMENTS FOR DISPLAYING AND VIEWING TOMOSYNTHESIS IMAGES

(71) Applicant: Real Time Tomography, LLC, Villanova, PA (US)

(72) Inventors: Susan Ng, Villanova, PA (US); Peter A. Ringer, Allentown, PA (US); Johnny Kuo, Lancaster, PA (US)

(73) Assignee: Real Time Tomography, LLC, Villanova, PA (US)

( * ) Notice: Subject to any disclaimer, the term of this patent is extended or adjusted under 35 U.S.C. 154(b) by 424 days.

(21) Appl. No.: 17/804,662

(22) Filed: May 31, 2022

(65) Prior Publication Data

US 2022/0292739 A1   Sep. 15, 2022

Related U.S. Application Data

(63) Continuation of application No. 16/816,386, filed on Mar. 12, 2020, now Pat. No. 11,361,479, which is a
(Continued)

(51) Int. Cl.
| | |
|---|---|
| *G06T 11/00* | (2006.01) |
| *A61B 6/02* | (2006.01) |
| *A61B 6/46* | (2024.01) |
| *G06T 7/00* | (2017.01) |
| *G06T 15/08* | (2011.01) |

(52) U.S. Cl.
CPC ............ *G06T 11/005* (2013.01); *A61B 6/025* (2013.01); *A61B 6/466* (2013.01); *G06T 7/0012* (2013.01); *G06T 15/08* (2013.01); *G06T 2200/04* (2013.01); *G06T 2207/30068* (2013.01); *G06T 2211/412* (2013.01); *G06T 2211/421* (2013.01); *G06T 2211/436* (2013.01)

(58) Field of Classification Search
CPC ..... G06T 11/005; G06T 7/0012; G06T 15/08; G06T 2200/04; G06T 2207/30068; G06T 2211/412; G06T 2211/421; G06T 2211/43; A61B 6/025; A61B 6/466
See application file for complete search history.

(56) References Cited

U.S. PATENT DOCUMENTS

| | | |
|---|---|---|
| 5,781,605 A | 7/1998 | Wohlrab |
| 6,381,349 B1 | 4/2002 | Zeng et al. |

(Continued)

OTHER PUBLICATIONS

Kuo, Johnny, et al. "Dynamic reconstruction and rendering of 3D tomosynthesis images." Medical Imaging 2011: Physics of Medical Imaging. vol. 7961. SPIE, 2011. (Year: 2011).*

(Continued)

*Primary Examiner* — Andrae S Allison
(74) *Attorney, Agent, or Firm* — Fox Rothschild LLP

(57) ABSTRACT

Systems and methods of enhanced display and viewing of three dimensional (3D) tomographic data acquired in tomosynthesis or tomography. A set of projection data is acquired with an image acquisition system and used to reconstruct enhanced 3D volume renderings that are viewed with motion, advanced image processing or stereotactically to assist in medical diagnosis. Various enhancements are provided for further processing the images, thereby providing additional features and benefits during image viewing.

36 Claims, 13 Drawing Sheets

Related U.S. Application Data continuation of application No. 14/776,435, filed as application No. PCT/US2014/030220 on Mar. 17, 2014, now Pat. No. 10,593,069.

(60) Provisional application No. 61/793,659, filed on Mar. 15, 2013.

(56) References Cited

U.S. PATENT DOCUMENTS

| | | | |
|---|---|---|---|
| 6,845,144 B2 | 1/2005 | Nishide et al. | |
| 7,653,229 B2 | 1/2010 | Kaufhold et al. | |
| 8,078,000 B2 | 12/2011 | Bohm et al. | |
| 8,233,690 B2 | 7/2012 | Ng et al. | |
| 2004/0066386 A1 | 4/2004 | Leprevost | |
| 2004/0070584 A1 | 4/2004 | Pyo et al. | |
| 2005/0226375 A1 | 10/2005 | Eberhard et al. | |
| 2006/0098856 A1 | 5/2006 | Botterweck et al. | |
| 2007/0036265 A1 | 2/2007 | Jing et al. | |
| 2007/0080686 A1* | 4/2007 | Dumoulin | G01R 33/56308 324/309 |
| 2007/0165769 A1 | 7/2007 | Goto et al. | |
| 2007/0172104 A1 | 7/2007 | Nishide et al. | |
| 2007/0258558 A1 | 11/2007 | Nishide et al. | |
| 2009/0274354 A1* | 11/2009 | Ng | A61B 6/4028 382/131 |
| 2010/0239064 A1* | 9/2010 | Zhou | G01N 23/04 382/131 |
| 2011/0293160 A1 | 12/2011 | Bruder et al. | |
| 2012/0020448 A1 | 1/2012 | Khare et al. | |
| 2012/0253169 A1* | 10/2012 | Guttman | G06T 15/08 600/410 |
| 2012/0256916 A1* | 10/2012 | Kitamura | G01S 17/89 345/419 |
| 2013/0030279 A1* | 1/2013 | Mistretta | A61B 5/004 600/410 |
| 2013/0336450 A1* | 12/2013 | Kyriakou | A61B 5/33 378/62 |
| 2014/0086467 A1* | 3/2014 | Song | G06T 11/006 382/131 |
| 2015/0201890 A1 | 7/2015 | Maidment et al. | |
| 2016/0042537 A1 | 2/2016 | Ng et al. | |
| 2016/0125584 A1* | 5/2016 | Suzuki | G06T 11/60 382/131 |

OTHER PUBLICATIONS

Wu, Tao, et al. "Digital tomosynthesis mammography using a parallel maximum-likelihood reconstruction method." Medical Imaging 2004: Physics of Medical Imaging. vol. 5368. SPIE, 2004. (Year: 2004).*

Schiemann, Thomas, et al. "Interactive 3D-segmentation of tomographic image volumes." Mustererkennung 1992: 14. DAGM-Symposium, Dresden, Sep. 14-16, 1992. Springer Berlin Heidelberg, 1992. (Year: 1992).*

* cited by examiner

The three points ($P_1$, $P_2$, $P_3$) define the reconstruction plane within the imaged volume.

Cutaway reconstruction represented by 3 ROI planes

ENHANCEMENTS FOR DISPLAYING AND VIEWING TOMOSYNTHESIS IMAGES

RELATED APPLICATIONS AND CLAIM OF PRIORITY

This patent document is a continuation of U.S. patent application Ser. No. 16/816,386 filed Mar. 12, 2020, which is a continuation of U.S. patent application Ser. No. 14/776,435 (U.S. Pat. No. 10,593,069) filed Sep. 19, 2015, which was the national stage filing of International Patent Application No. PCT/US2014/030220 filed Mar. 17, 2014, which claims priority to U.S. Provisional Application No. 61/793,659 filed Mar. 15, 2013. The contents of each priority application are fully incorporated into this document by reference.

BACKGROUND

The present disclosure is related to the field of image reconstruction and display. More specifically, the present disclosure is related to rendering and displaying images from digital x-ray tomosynthesis or tomography.

Tomography refers to imaging by sections or sectioning an object into multiple images, and reconstructing the images to view an object of interest. In digital tomosynthesis, one or more x-ray sources and one or more one-dimensional or two-dimensional (2D) x-ray digital detectors are used to acquire a set of projection radiographs of the object. One advantage of tomosynthesis is that it removes the overlapping tissue that can obscure clinical indications or cause false positives. In digital breast tomosynthesis, clinical studies have shown that tomosynthesis is more sensitive and specific than mammography.

During diagnostic review of medical images, the clinician examines the images for abnormalities, fractures, indications of cancer, and other related observable occurrences. The clinician may request additional images to be taken at different angles to better view suspicious areas. In the case of lesions (e.g., masses, distortions and calcifications), the shape or morphology determines the likelihood of the lesion being benign or malignant. In the case of a fracture, the type and location of the fracture will determine the treatment.

Tomosynthesis, as a 3D imaging modality, inherently has the geometric information necessary to reconstruct images at various angles and planes. Instead of acquiring new images, additional images can be reconstructed at different angles using existing tomosynthesis projection data, thereby reducing radiation exposure to the patient. Advanced 3D volume reconstructions that improve the display of the anatomy and, thus the clinician's diagnostic assessment, are also possible in tomosynthesis. However, the conventional method for displaying and viewing tomosynthesis images is to reconstruct a stack of image slices at fixed increments (e.g. 1 mm for tomosynthesis to 3 mm for CT) parallel to the detector which are then reviewed at a later time. This method limits further interrogation and more detailed assessment of the image data.

A method of dynamic reconstruction and rendering of three-dimensional (3D) tomographic images is discussed in U.S. Pat. No. 8,233,690, the content of which is hereby incorporated by reference in its entirety. U.S. Pat. No. 8,233,690 teaches a method of image reconstruction referred to as dynamic reconstruction and rendering (DRR). In DRR, a single image is reconstructed from the projection data in real-time and on-demand. An image can be reconstructed for a region of interest, at any depth and with any reconstruction and processing parameters. The DRR method uses a fast, back-projection filtering method that supports the ability to provide enhanced display and viewing capabilities in tomosynthesis. However, any fast 3D image reconstruction method (i.e. a back projection or iterative method) that is responsive to the user can be used. The reconstruction method can be implemented on a CPU, GPU, FPGAs or any other graphical device.

This document describes methods, systems and components that expand upon the previous DRR methods as disclosed in U.S. Pat. No. 8,233,690.

SUMMARY

In various embodiments, the present disclosure provides systems and methods of enhanced display and viewing of three dimensional (3D) tomographic data acquired in tomosynthesis or tomography. A set of projection data is acquired with an image acquisition system and used to reconstruct enhanced 3D volume renderings that are viewed with motion, advanced image processing or stereotactically to assist in medical diagnosis.

In one sample embodiment, the present disclosure teaches a method for dynamically reconstructing 3D tomographic images from a set of projection images. The method includes loading a set of projection images into a memory device, determining a reconstruction method for the set of projection images, reconstructing a 3D tomographic image from the set of projection images to be displayed to a user, rendering and displaying the reconstructed 3D tomographic image and providing one or more enhancements for advanced image processing and manipulation of 3D tomographic data included within the reconstructed 3d tomographic image.

Additionally or alternatively, in the method as described above, the one or more enhancements includes at least providing progressive image load and reconstruction. Additionally or alternatively, the progressive image load and reconstruction further includes acquiring a data set comprising a plurality of projection images, performing an asynchronous projection load of the data set, and determining if the data set is loaded. If the data set is loaded, the method can additionally include performing full reconstruction, post-processing and displaying of the plurality of projection images. If the data set is partially loaded, the method can additionally include performing a partial reconstruction, displaying the partial reconstruction, determining whether to load another projection image, and, if the processing device determines to load another projection image, performing an asynchronous load on the next projection image.

Additionally, or alternatively, the method as described above further includes providing 2D projection image and 3D tomosynthesis image co-registration. Additionally or alternatively, providing 2D projection image and 3D tomosynthesis image co-registration further includes displaying display projection and tomosynthesis images that are spatially co-registered in an imaged volume at a same z-depth and orientation.

Additionally, or alternatively, the method as described above further includes providing dynamic filtering. Additionally or alternatively, the dynamic filtering can include a set of parameters that are defined as a filtering set and applied after reconstruction.

Additionally, or alternatively, the method as described above further includes defining an image reconstruction plane having three points in an imaged volume. Additionally or alternatively, defining an image reconstruction plane having three points in an imaged volume can include receiving, from a user, an indication of three points on a displayed image volume and reconstructing the image volume by aligning a reconstruction plane to a plane defined by the three points as selected by the user.

Additionally, or alternatively, the method as described above further includes integrating a compass into a displayed image. Additionally or alternatively, integrating a compass into a displayed image includes determining a boundary of an anatomy contained detailed within at least one of the projection images and the tomosynthesis image, determining a thickness of the anatomy, creating a compass using an outline of the anatomy and scaling the compass accordingly, and reconstructing an updated image at a central slice location incorporating the compass.

Additionally, or alternatively, the method as described above further includes providing super-resolution magnification glass. Additionally or alternatively, providing the super-resolution magnification glass can include receiving a user-selected region from a reconstructed image, magnifying the user-selected region by determining sub-pixel shifts between multiple projection images related to the reconstruction image and displaying a magnification view of the user-selected region.

Additionally, or alternatively, the method as described above further includes providing a 3D volume reconstruction for a region of interest. Additionally or alternatively, providing a 3D volume reconstruction for a region of interest can include receiving a user-selected location for magnification of a reconstructed image, defining a region of interest based upon the user-selected location for magnification, reconstructing a magnified image based upon the region of interest from a set of projection images related to the reconstruction image, wherein the magnified image has a magnification level greater than the reconstructed image, overlaying the magnified image on the reconstruction image to produce a combination image and displaying the combination image.

Additionally, or alternatively, the method as described above further includes providing 3D reconstruction for a region of interest within a reconstructed image. Additionally or alternatively, providing 3D reconstruction for a region of interest within a reconstructed image can include reconstructing a maximum intensity projection by changing one or more plane orientations of reconstructed slices used to generate the reconstruction image.

Additionally, or alternatively, the method as described above further includes providing a 3D cut-away. Additionally or alternatively, providing a 3D cutaway can include removing surface elements of a 3D volume to make internal features visible within the 3D volume while also presenting 3D spatial information related to the 3D volume.

Additionally, or alternatively, the method as described above further includes providing stereoscopic tomosynthesis. Additionally or alternatively, providing stereoscopic tomosynthesis can include combining two tomograms, wherein each tomogram is angled and selectively displayed to either a viewer's right or left eye in stereo.

Additionally, or alternatively, the method as described above further includes providing a four-dimensional tomographic display. Additionally or alternatively, providing a four-dimensional tomographic display can include loading a set of projection images, adjusting a time point and subset size for the set of projection images, selecting a projection set based upon the adjusted time point and subset size, reconstructing a projection image based upon the selected projection set, performing any post processing on the projection set, displaying the projection set, determining any updates to apply to the projection set, if the updates to the projection set are temporal updates, adjusting the time point associated with the projection set and if the updates to the projection set are not temporal, adjusting one or more reconstruction parameters for the projection set and reconstructing the projection image accordingly.

Additionally, or alternatively, the method as described above further includes providing a hybrid dynamic reconstruction. Additionally or alternatively, providing a hybrid dynamic reconstruction can include initially displaying a cached set of pre-reconstructed static slices and performing dynamic reconstruction when requested by a user to view information outside of the pre-constructed static slices.

Additionally, or alternatively, the method as described above further includes providing a non-planar reconstruction.

Additionally, or alternatively, the method as described above further includes dynamically reconstructing a super-resolution image.

Additionally, or alternatively, the method as described above further includes filtering one or more images having super-resolution zoom.

Additionally, or alternatively, the method as described above further includes dynamically adjusting, by a processing device, one or more filters to account for changing spatial frequencies in the one or more super-resolution zoomed images.

Another sample embodiment includes a system for providing enhancements for displaying one or more tomosynthesis images. The system can include a processing device and a non-transitory computer readable medium operably connected to the processing device and configured to store one or more instructions that, when executed, cause the processing device to perform various functions. For example, the system may be configured to perform the various methods as described above.

DETAILED DESCRIPTION

This disclosure is not limited to the particular systems, devices and methods described, as these may vary. Also, the terminology used in this document is only for the purpose of describing the particular versions or embodiments only, and it is not intended to limit the scope.

As used in this document, the singular forms "a," "an," and "the" include the plural reference unless the context clearly dictates otherwise. Unless stated otherwise, references to "or" are intended to be inclusive, meaning that they include one or the other as alternatives or more than one of the associated terms together. Also, the term "comprising" as used herein means "including, but not limited to."

The present disclosure is directed to systems and methods for enhancing displaying and viewing tomosynthesis images, for example, displayed using the dynamic reconstruction and rendering (DRR) as taught by U.S. Pat. No. 8,233,690. As described herein, the enhancements may include various tools and features for advanced image processing and manipulation for three-dimensional (3D) tomographic data acquired in tomosynthesis or tomography. For example, the various enhancements may include, but are not limited to, progressive image load and reconstruction, two-dimensional (2D) projection image and 3D tomosynthesis image co-registration, dynamic filtering, defining an image reconstruction plane with three points in an imaged volume, integrating a compass into a displayed image, providing super-resolution magnification glass, providing 3D volume reconstruction for a region of interest (ROI), providing a 3D cut-away, providing stereoscopic tomosynthesis, providing a four-dimensional (4D) tomographic display, providing a hybrid dynamic reconstruction, providing non-planar reconstruction, and dynamically reconstructing a super-resolution image for a ROI to a screen. Each of these sample enhancements are described in greater detail herein.

One potential enhancement, as listed above, may be to provide progressive image load and reconstruction. For dynamic reconstruction and rendering, the load time can be very long if an image dataset is very large. A progressive load and reconstruction technique may reduce the relative wait time to the user by providing the user with a partial reconstruction before all the projection image data is loaded. As more projection data is loaded, the displayed reconstruction is progressively updated and refined until all the projection image data is loaded.

Figure 1:
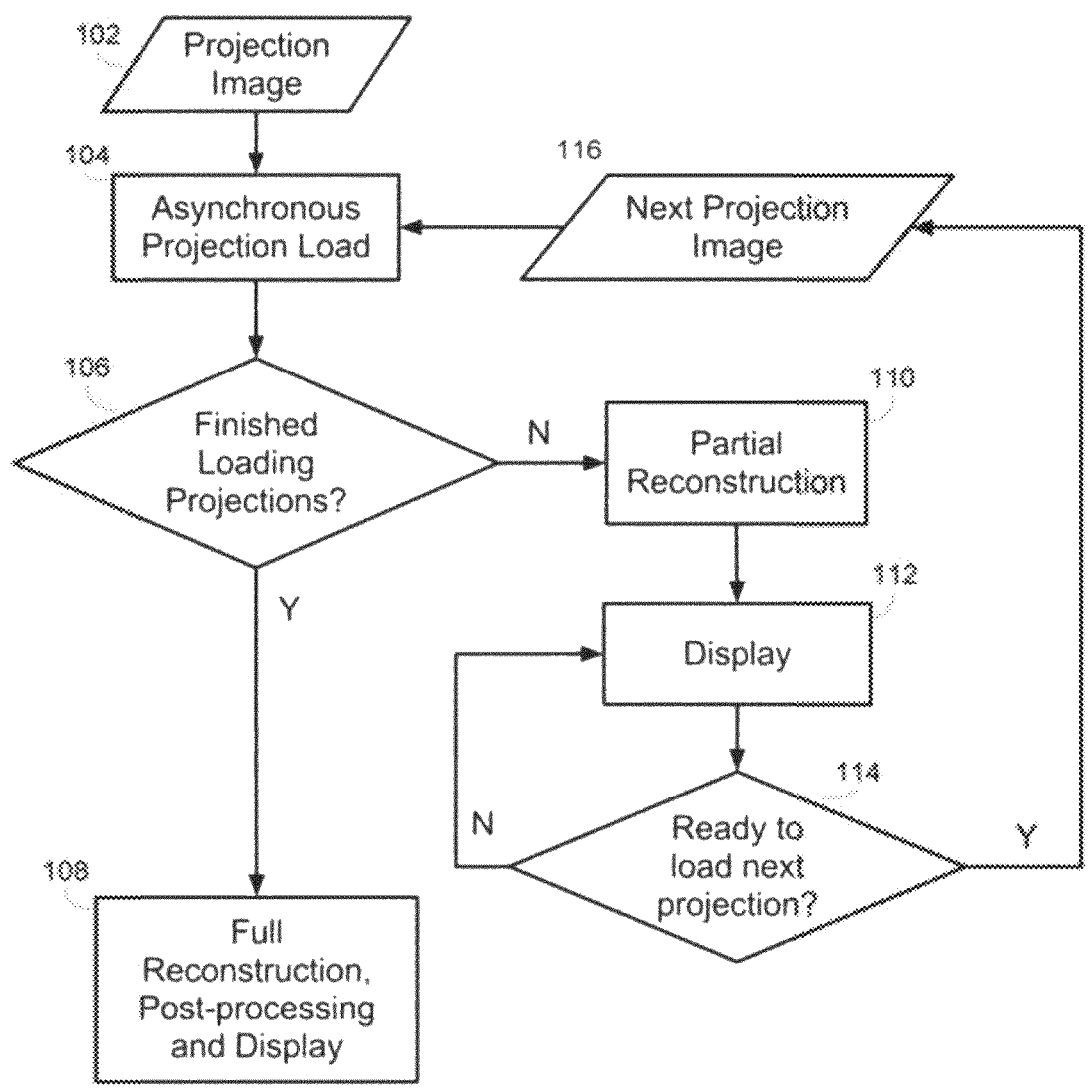
FIG. 1 illustrates a flowchart showing a sample process for progressive image load and reconstruction.

FIG. 1 illustrates a flowchart showing a sample process for progressive image load and reconstruction. A processing device may acquire a projection image 102, and begin an asynchronous projection load 104. The processing device may determine 106 if it has finished loading the projections in the data set. If the processing device has finished, the processing device may perform 108 full reconstruction, post-processing and display the images. Post-processing may include image filtering, pixel inversion, flipping the image about the vertical and horizontal axis, rotation, statistical conditioning such as de-noising, as well as changing a window width and window level thereby adjusting gray levels of an image However, if the processing device determines 106 it has not finished loading the projections, the processing device may perform 110 a partial reconstruction and display 112 the partial reconstruction. The processing device may then determine 114 if it is ready to load the next projection. If the processing device is not ready, the process may return to displaying 112 the partially reconstructed image. If the processing device does determine 114 that it is ready to load the next projection, the processing device may proceed to the next projection image 116, and the process as shown in FIG. 1 repeats.

Progressive image load and reconstruction may be implemented in various embodiments. For example, a simple reconstruction may be started with a single projection, and then a second is added, then a third, and so on until the dataset is complete. This may provide someone with the ability to begin reconstruction with a partial dataset (possibly even starting with one projection), and display the partial reconstruction asynchronously while the other projection images are loading. As more projection images are loaded, the partial reconstruction may be updated. This technique may also allow for loading a few projections and reconstructing every n-th pixel (rough tiling). When using this technique, the processing device may be further configured to display an indication that the full image set has not finished reconstructing, so as to inform someone viewing the images that additional information may be loading.

Another potential enhancement, as listed above, may be to provide 2D projection image and 3D tomosynthesis image co-registration. Co-registration, as described herein, may display projection and tomosynthesis images spatially co-registered in the imaged volume at the same z-depth and orientation. The imaged volume may be defined by the image acquisition system. Most conventional medical review workstations display a reconstructed tomosynthesis image corresponding to a z-depth in the imaged volume. If the workstation allows display of the projection image, the projection image is then shown full-screen (stretch to fit) on the screen. There is no correlation between how the tomosynthesis and projection images are displayed.

Figure 2:
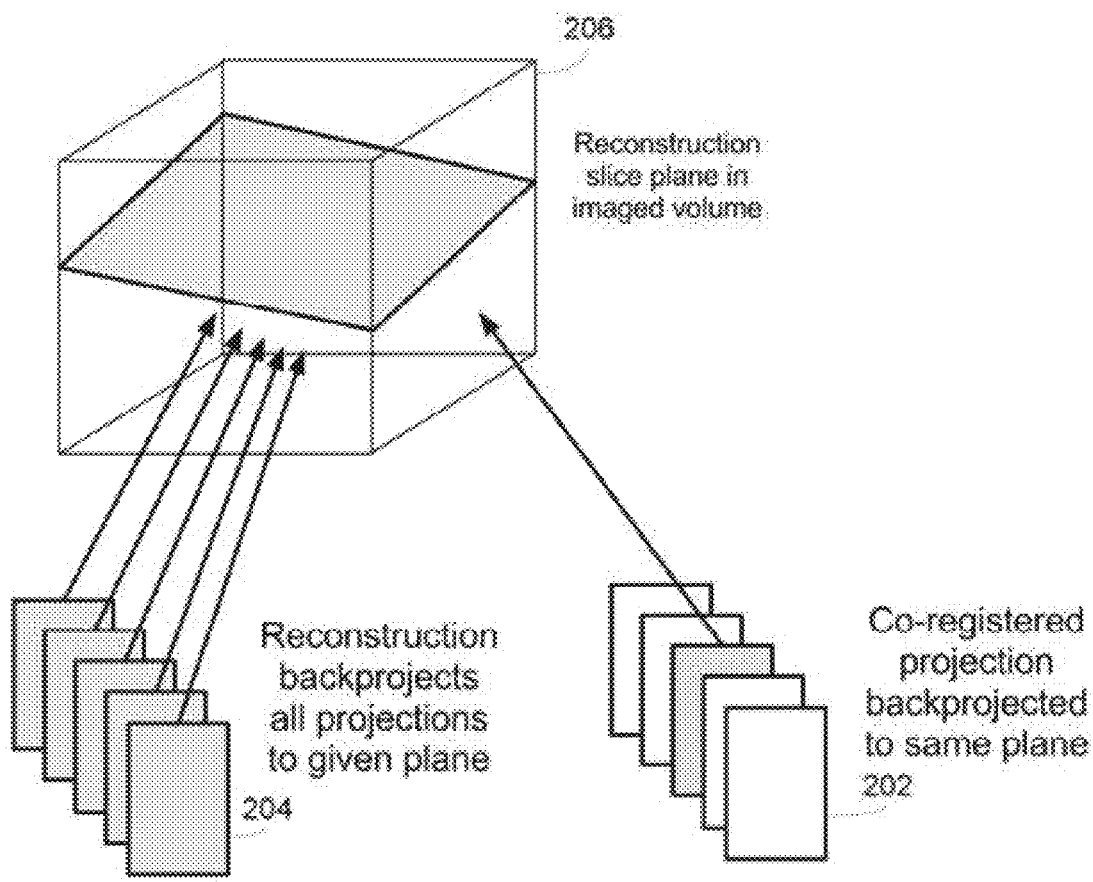
FIG. 2 illustrates an example of two-dimensional image and three-dimensional image co-registration.

As shown in FIG. 2, by co-registering the projection 202 and reconstructed images 204 at the same z-depth and orientation, the observer can determine the contribution of each projection image to objects that are in focus in the reconstructed image 206. This co-registration helps the clinician in distinguishing tissue and lesions from artifacts that may arise from the reconstruction or image processing.

To provide co-registration, in one example embodiment, a processing device may display reconstructed image at a given plane position and orientation. Before displaying the projection image, the processing device may back-project the projection image to the same position and orientation as the reconstructed plane while keeping the back-projected projection image in memory. The processing device may repeat this for all projection images. Once displayed, a user may scroll through the projection images, and objects that are in focus in the reconstructed image will appear to rotate.

Another potential enhancement, as listed above, may be to provide dynamic filtering. A number of GPU manufacturers have implemented filtering functions within the graphics hardware. These include convolution, unsharp masking and fast Fourier filtering. Alternatively, customized filters may be implemented as shader programs and applied to the image as it passes through the GPU pipeline. This may be done by rendering the image to a temporary texture pixel for pixel using an orthographic projection geometry. Dynamic filtering may allow the user to change the image presentation by changing the post-reconstruction filters on the fly by using of a set of filter parameters that are defined as a set and applied dynamically after reconstruction. The various reasons for dynamically changing the filters include, but are not limited to, one or more of: to provide for different user-preference; to improve the presentation based on information of the breast (i.e. tissue density); to improve the presentation of certain objects (i.e. masses, calcifications); to compensate for different image acquisition systems or detectors; to compensate for radiation dose.

Figure 3:
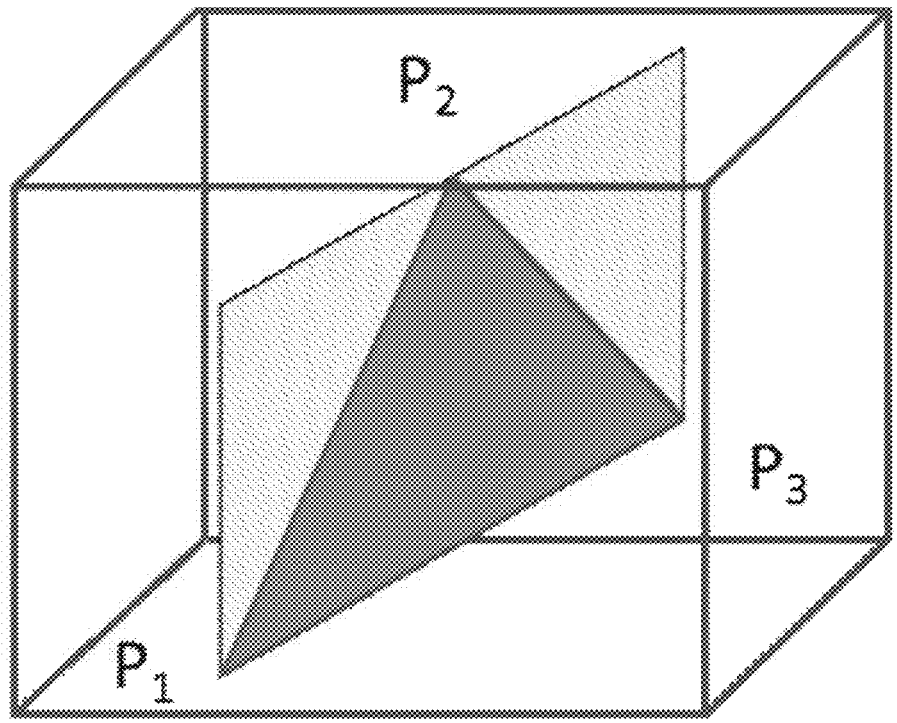
FIG. 3 illustrates an example reconstruction plane defined within an image volume.

Another potential enhancement, as listed above, may be to define an image reconstruction plane with three points in an imaged volume. As shown in FIG. 3, the reconstruction plane of an image can be defined by 3 points in the imaged volume. To create the reconstruction plane, according to an embodiment, three points in the valid volume space may be selected. A user may use a pointing device to select each point P[x, y, z]. For example, the user may select each point by selecting the point on a scale model of the imaged volume, or by scrolling to a desired z-depth and selecting an (x, y) location on the displayed image. Once the three unique points have been selected, the processing device may reconstruct the image, aligning the reconstruction plane to the plane defined by the three points. If the plane cannot be created within the imaged volume, the processing device may not reconstruct the image.

Another potential enhancement, as listed above, may be to provide a compass. The compass may be a graphic user interface (GUI) object that shows the imaged volume and the location and orientation of the reconstruction plane of the image that is currently displayed on the screen. The compass can be a generic geometric shape (i.e. rectangular prism) that represents the imaged volume or a model of the anatomy that is being imaged. In the instance of breast imaging, the compass models the breast under compression during imaging.

Figure 4:
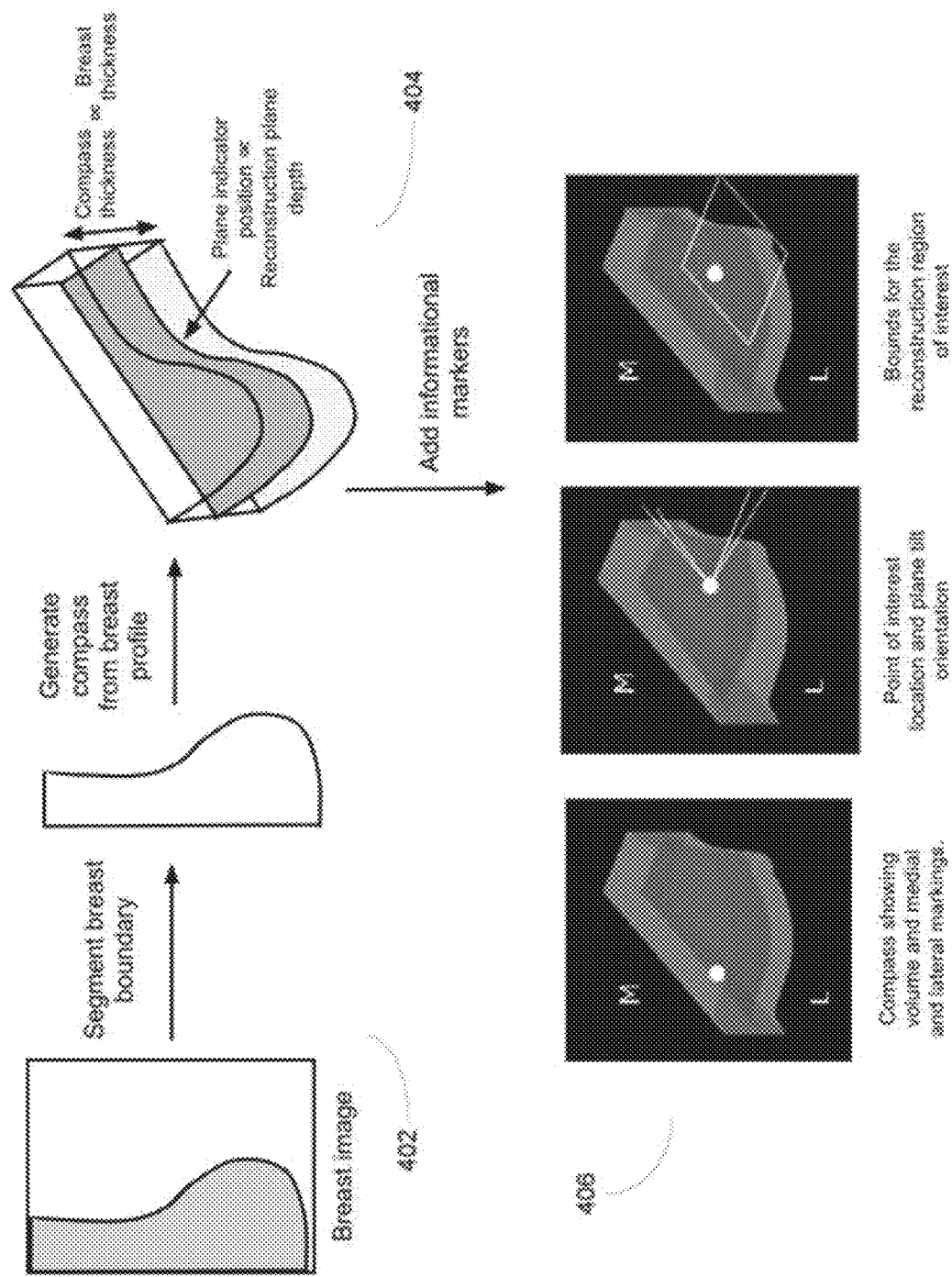
FIG. 4 illustrates a flowchart showing a sample process for creating a compass within an image.

FIG. 4 illustrates a sample process for creating the compass. Initially, a processing device may determine 402 the boundary of the anatomy from either the projection images or the tomosynthesis image. If the projection images are 2D, the central projection is preferable as it will give the fullest profile. The boundary profile can be determined by a number of available boundary detection methods, such as Otsu's method, that are available. The processing device may further determine 404 the thickness of the anatomy, either reported by the image acquisition system or retrieved from the DICOM header. The processing device may create the compass using the anatomy outline and thickness and scale the dimensions to the compass accordingly. The processing device may then reconstruct 406 an image at a central slice location in the valid thickness incorporating the compass. The processing device may further copy central slice reconstruction onto compass reconstruction plane indicator, display a center of rotation or point of interest (POI), add axes and calipers from the 0 degrees at the POI, and add a box showing where reconstructed ROI is within imaged volume.

Another potential enhancement, as listed above, may be to provide a providing super-resolution magnification glass. Most conventional review workstations provide a magnification box or glass that will magnified an area of the image currently displayed on the screen. Typically, the magnification is a digital zoom in which an area of the image is cropped and then enlarged. Interpolation is normally applied to the enlarged image to reduce the pixilation caused by the image enlargement.

Figure 5:
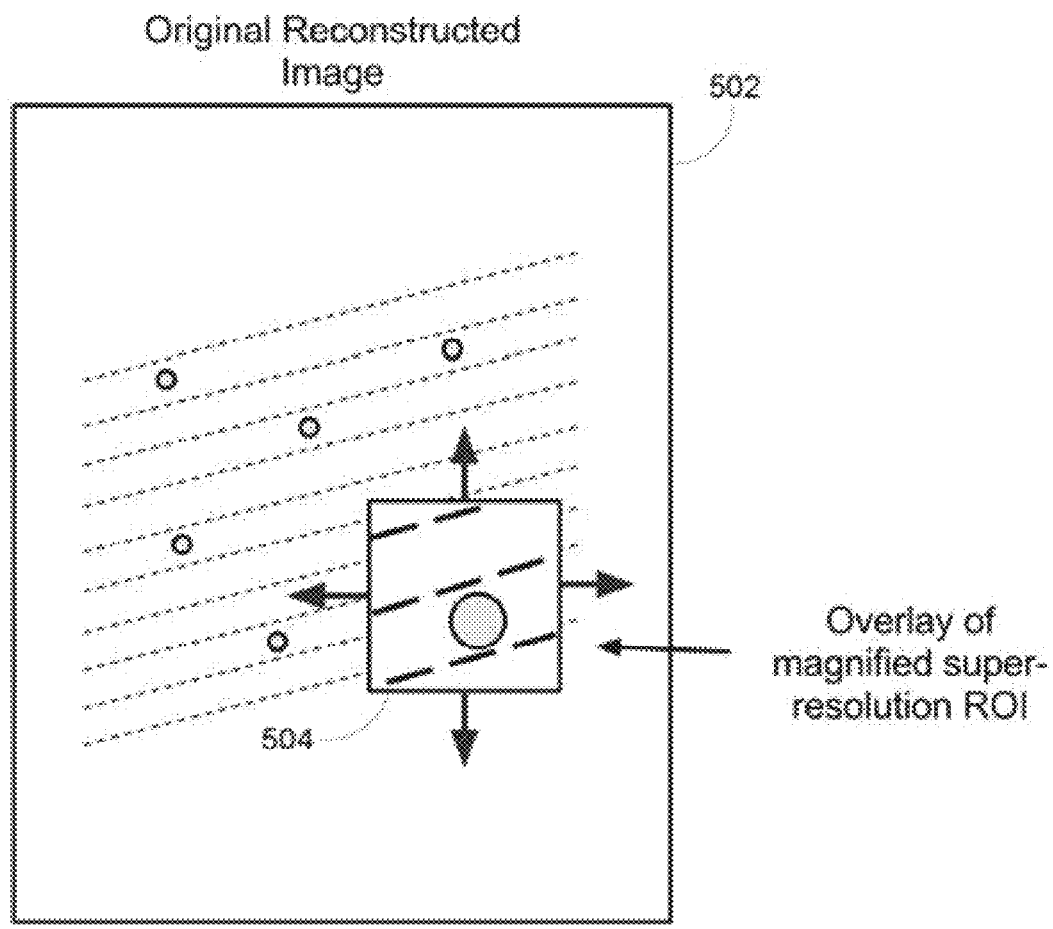
FIG. 5 illustrates a sample of an overlay of a magnified super-resolution region of interest.

Super-resolution is the enhancement of the image resolution beyond the resolution of the detector that acquires the images. In tomosynthesis, super-resolution is possible because multiple projection images are acquired of the object. The sub-pixel shifts between the multiple projection images results in greater spatial information per pixel in the final reconstruction. The Super-Resolution magnification glass applies the principles of super-resolution to a region of interest. The effect is similar to an optical zoom in that it provides magnification without a loss in resolution or image quality. For example, as shown in FIG. 5, a user may opt to select a region 504 from reconstructed image 502, and the super-resolution magnification techniques as described herein may provide a high quality magnification of region 504.

Figure 6:
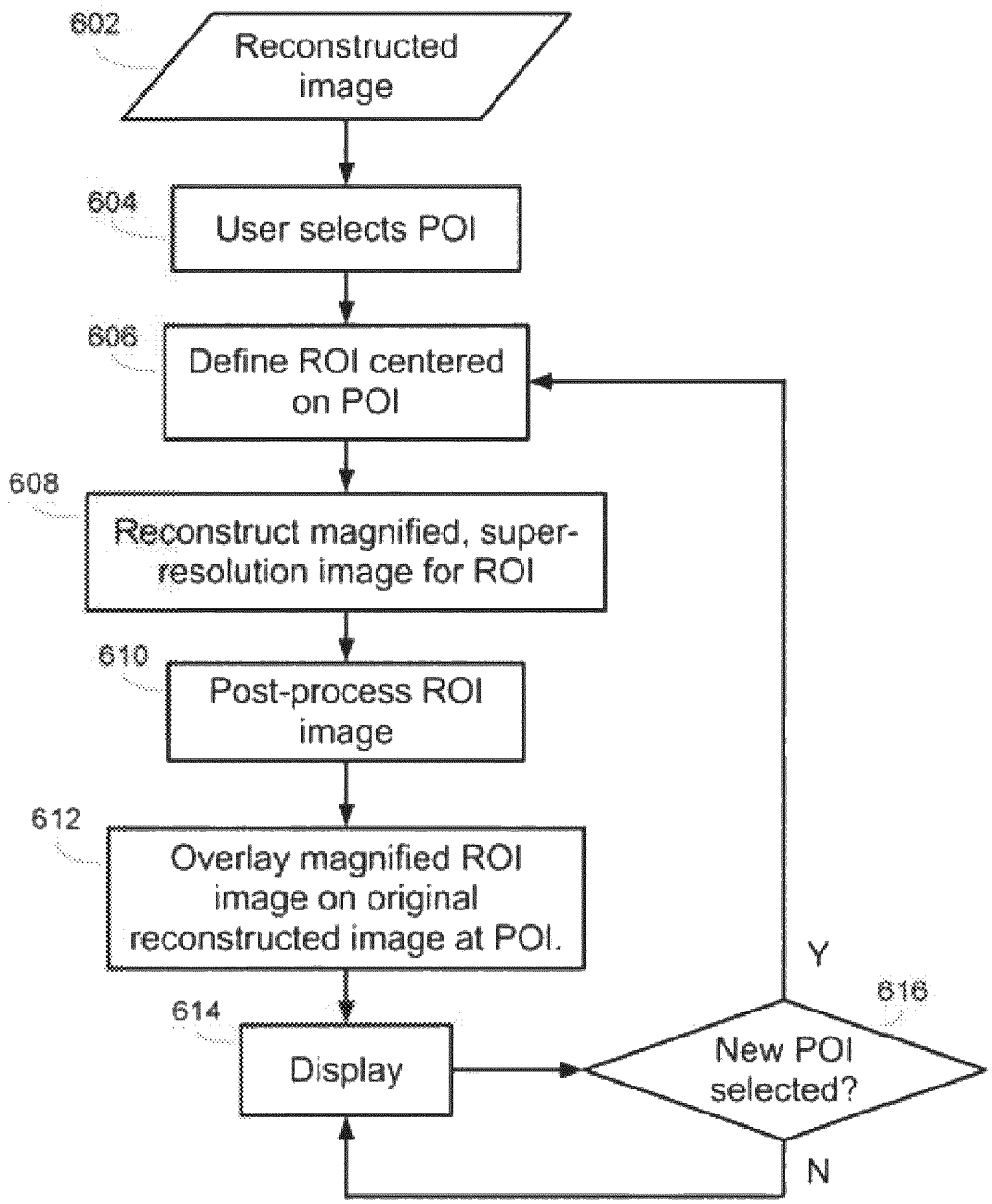
FIG. 6 illustrates a flowchart showing a sample process for displaying a super-resolution region of interest.

FIG. 6 illustrates a flowchart showing a sample process for displaying a super-resolution magnification. The processing device may start 602 with a 3D image reconstructed to a default zoom level, typically 1.0, displayed on the screen. A user may use a pointing device or other similar selection device to select 604 the location of the magnification within the displayed image, and the processing device may define 606 a ROI centered at the user-defined location.

The processing device may reconstruct 608 the 3D image from the projection images for the ROI at a zoom level greater than the default zoom level (i.e. greater than 1.0), and may perform 610 any post-processing on the reconstructed image. The processing device may place reconstructed ROI image at the user-defined location, overlaying 612 it on the displayed image, and the display 614 the magnified image. The processing device may monitor and determine 616 any changes in the user location as defined by the pointing device. If the user-defined location or z-depth changes (greater than some minimum value), the processing device may remove the existing ROI image and reconstruct new ROI image at the new user location.

Figure 7:
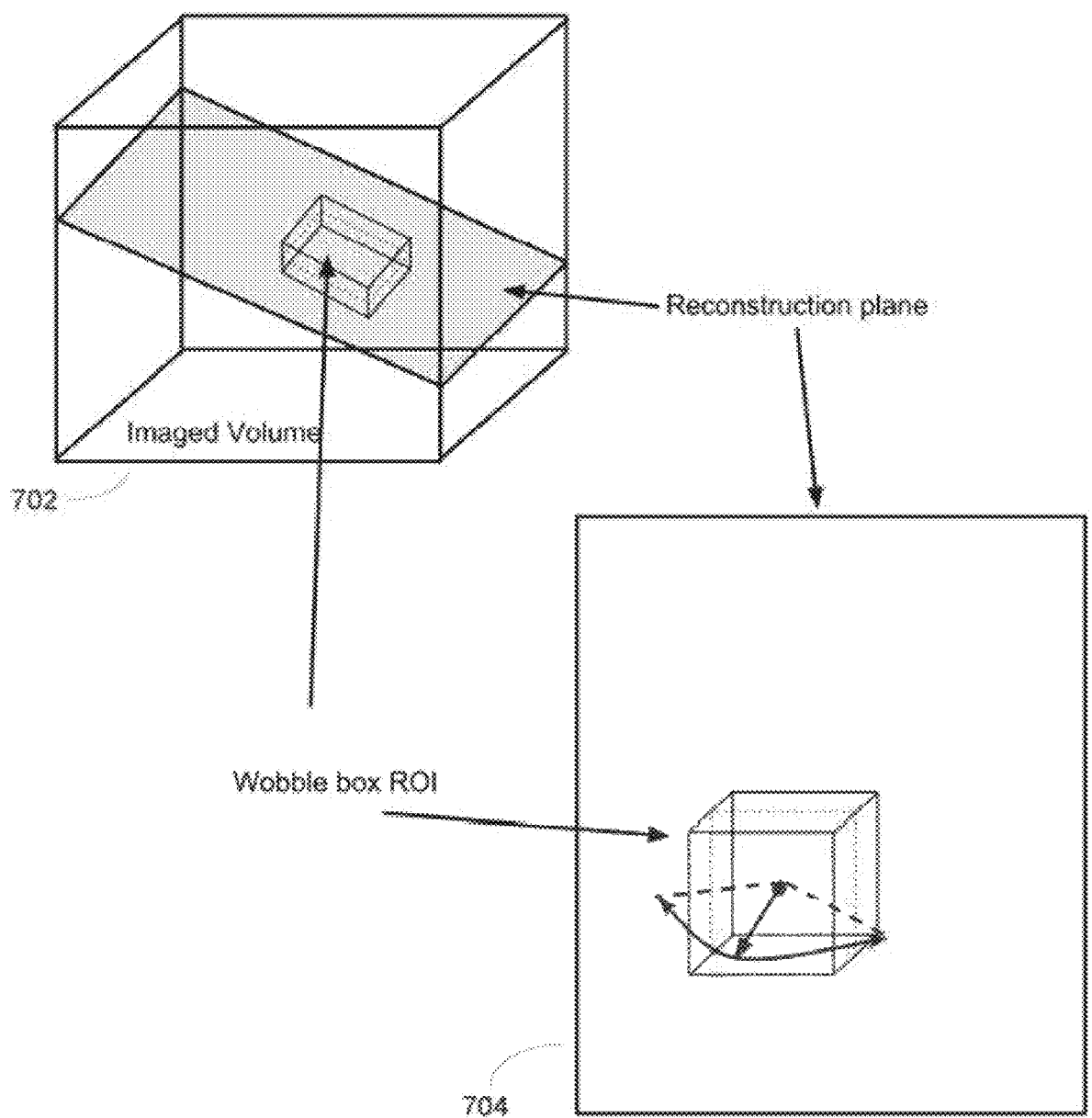
FIG. 7 illustrates an example of a wobble box according to an embodiment described herein.

Another potential enhancement, as listed above, is providing 3D volume reconstruction for a region of interest (ROI) to create a "wobble box". The wobble box is a 3D volume reconstruction for a ROI that can be rotated for a limited range of angles. As shown in FIG. 7, the 3D volume 702 can be reconstructed as a slab or maximum intensity projection (MIP) 704. Wobbling is simulated by changing the plane orientations of the reconstructed slices used to generate the volume. In tomosynthesis, the angular range of the wobble box is limited to avoid visual artifacts as tomosynthesis spatial resolution is non-isotropic.

To create a wobble box, according to an embodiment, a processing device may start with a 3D image reconstructed to a given zoom level, typically 1.0, displayed on the screen. A user may use a pointing device to define a location for the wobble box in the displayed image, and the processing device may define a ROI centered at the user-defined location. The processing device may construct a 3D volume for that ROI with volume centered at a same z-depth as the original displayed reconstructed image. This is what is referred to herein as the wobble box.

The processing device may define a normal vector for the wobble box, typically starting at the same normal direction as the original displayed reconstructed image, and reconstruct several slices at different locations along the wobble box normal to generate the volume rendering within the wobble box. The processing device may place wobble box at the user-defined location, overlaid on displayed image. To rotate or wobble the ROI volume, the processing device may, in response to a user selection, change the normal direction of the wobble box. The processing device may monitor changes to current location of the pointing device. If the pointing device location changes (greater than some minimum value), the processing device may map the location changes to rotation of the normal direction of the wobble box. The processing device may remove existing wobble box from the displayed image and reconstruct wobble box at new angle. Various other features may be incorporated as well. For example, the processing device may limit the tilt of wobble box normal to avoid artifacts. Similarly, rotation of the wobble box may be controlled by either user selection, or performed automatically by the processing device.

Figure 8:
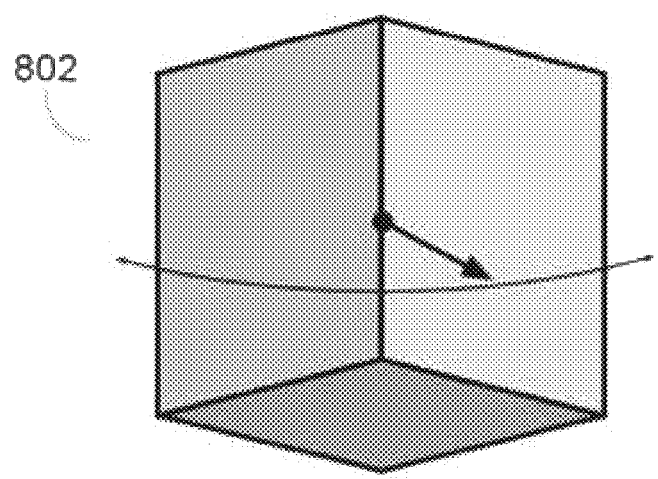
FIG. 8 illustrates a three-dimensional cut-away.

Another potential enhancement, as listed above, is providing a 3D cut-away. For example, as shown in FIG. 8, a 3D cut-away 802 removes the surface elements of a 3D volume to make the internal features visible while still presenting 3D spatial information. Creating the cut-away view involves creating 3 separate reconstructions oriented at different angles and stitching them together.

To create a 3D cut-away, according to an embodiment, a processing device may start with a 3D image reconstructed to a given zoom level, typically 1.0, displayed on the screen. A user may use a pointing device to specify a location in the displayed image to place the 3D cut-away. The processing device may define 3 ROI whose planes intersect in the imaged volume at the user-defined location. The intersection angle between the cutaway planes will typically be 90 degrees, but may be other values to accommodate more flexible visualization of the anatomy of interest and to account for angular limits imposed by the projection acquisition angles. The processing device may create slice reconstructions or 3D volume reconstructions (i.e. slab or MIP) for each ROI plane. The processing device may create the cut-away for a ROI or fill the entire screen, add lines to visually delineate cutaway plane intersections, and display the 3D cut-away. Because tomosynthesis has non-isotropic spatial resolution, none of the 3 ROI planes may be orthogonal to the direction of acquisition.

Figure 9:
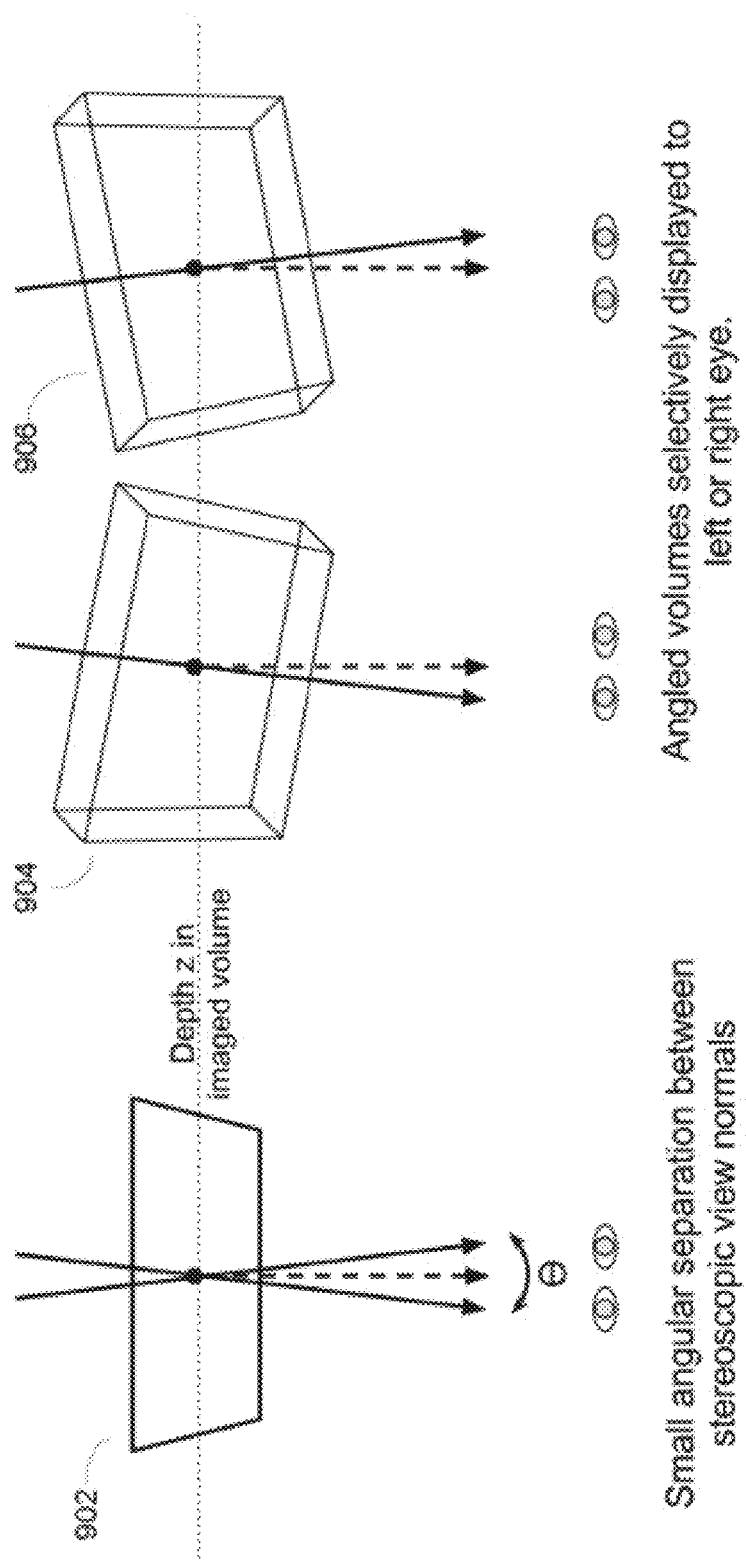
FIG. 9 illustrates a sample set of images for stereoscopic tomosynthesis.

Another potential enhancement, as listed above, is providing stereoscopic tomosynthesis. As shown in FIG. 9, a tomogram 902 reconstructed from 2D projection images provides a cross-sectional view of a 3D volume. However, the tomogram provides no perception of depth or perspective. Stereoscopic tomosynthesis provides the perception of three-dimensional depth from two tomograms 904 and 906, each angled and selectively displayed to either a viewer's right or left eye. Stereo tomosynthesis requires a display device capable of isolating which eye is receiving which image, either with glasses or directional backlighting.

Figure 10:
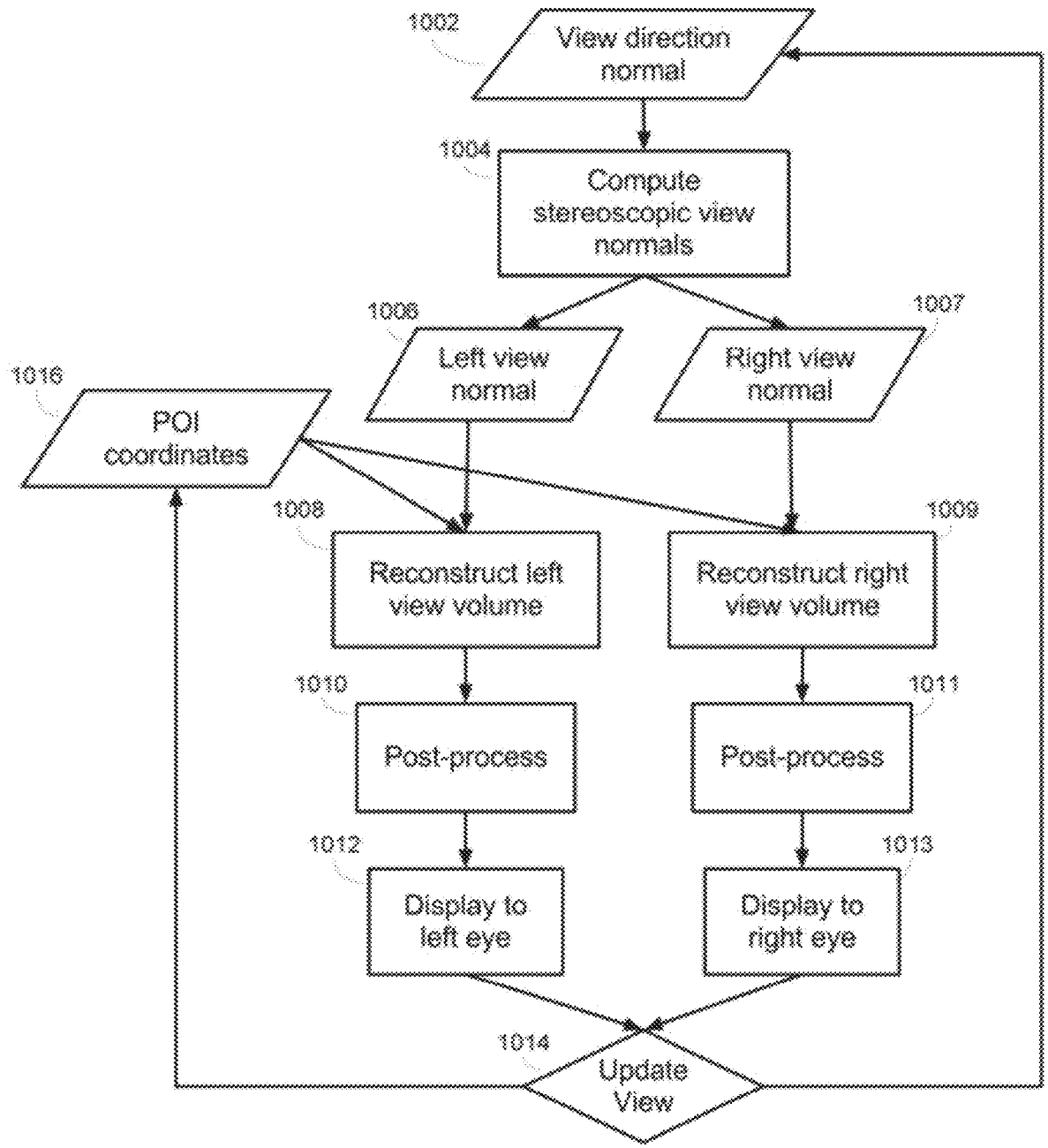
FIG. 10 illustrates a flowchart showing a sample process of creating a stereoscopic tomosynthesis image.

FIG. 10 illustrates a flowchart showing a sample process of creating a stereoscopic tomosynthesis image. Initially, the processing device may load or display an image in the normal direction 1002. The processing device may compute 1004 a set of stereoscopic view normals in order to reconstruct a pair of 3D volumes (either slab or MIP) centered at a given z-depth. The 3D volumes will have normals with sufficient angular separation to generate a stereoscopic effect, typically in the 3-5 degree range. The processing device may load 1006 a left view normal as well as load 1007 a right view normal. The processing device may reconstruct 1008 the left view volume, and perform 1010 any post-processing on the imaged volume. Similarly, the processing device may reconstruct 1009 the right view volume, and perform 1011 and post-processing on the imaged volume.

The processing device may selectively display the appropriate reconstruction to the viewer's left 1012 or right eye 1013. This can be done using various methods. For example, the reconstructions can be alternately displayed in quick succession in combination with shutter glasses or polarized glasses. Alternatively, the reconstructions can be displayed simultaneously using an autostereoscopic display.

In response to any changes by the user of the z-depth, both volumes reconstructions will need to be dynamically updated 1014. The processing device may determine 1016 the changed coordinates and the reconstruction process as described above may repeat.

Another potential enhancement, as listed above, is providing a four-dimensional tomographic display incorporating a measure of time. The 4D time-varying tomographic acquisition technique is basically a tomographic acquisition with the addition of having different time points at each of the projection angles. Each projection image is acquired at a different time and at a particular projection angle. By acquiring projections over time in this manner, it is possible to perform a reconstruction with dynamic time information. Applications for time-varying tomosynthesis reconstruction include the visualization of contrast enhancement dynamics or tracking a biopsy needle position.

To do the time-varying reconstruction, the reconstructions are generated from a subset of the projection images. The projections in the subset are chosen to optimize angular span and include projections with appropriate acquisition times to generate the reconstruction at the desired time point. The example shown below illustrates an example of the projection image subsets which could be used for an acquisition where the gantry swings in a single direction to acquire N projections and resets to the start position to acquire projection N+1.

| Time point | Projections in subset |
| --- | --- |
| 0 | 0, 1, 2, 3, 4, 5, 6, 7, 8 |
| 1 | 9, 1, 2, 3, 4, 5, 6, 7, 8 |
| 2 | 9, 10, 2, 3, 4, 5, 6, 7, 8 |
| 3 | 9, 10, 11, 3, 4, 5, 6, 7, 8 |
| 4 | 9, 10, 11, 12, 4, 5, 6, 7, 8 |

It is also possible to vary the projection image subset size to improve the temporal dynamism of the 4D tomosynthesis reconstruction. With one projection image being updated per timepoint update, there is a 1/N averaging effect from the backprojection reconstruction since there is only one projection worth of updated time information. To reduce the time-averaging effect, a smaller number of projection images can be used in the subset. If we shrink the subset from the previous example, we would have the following subsets:

| Time point | Projections |
| --- | --- |
| 0 | 0, 1, 2, 3, 4, 5, 6, x, x |
| 1 | x, 1, 2, 3, 4, 5, 6, 7, x |
| 2 | x, x, 2, 3, 4, 5, 6, 7, 8 |
| 3 | 9, x, x, 3, 4, 5, 6, 7, 8 |
| 4 | 9, 10, x, x, 4, 5, 6, 7, 8 |

In the above example, dropping 2 projections from the 9 projection subset during each time update would reduce the time-averaging effect from 1/9 to 1/7.

Figure 11:
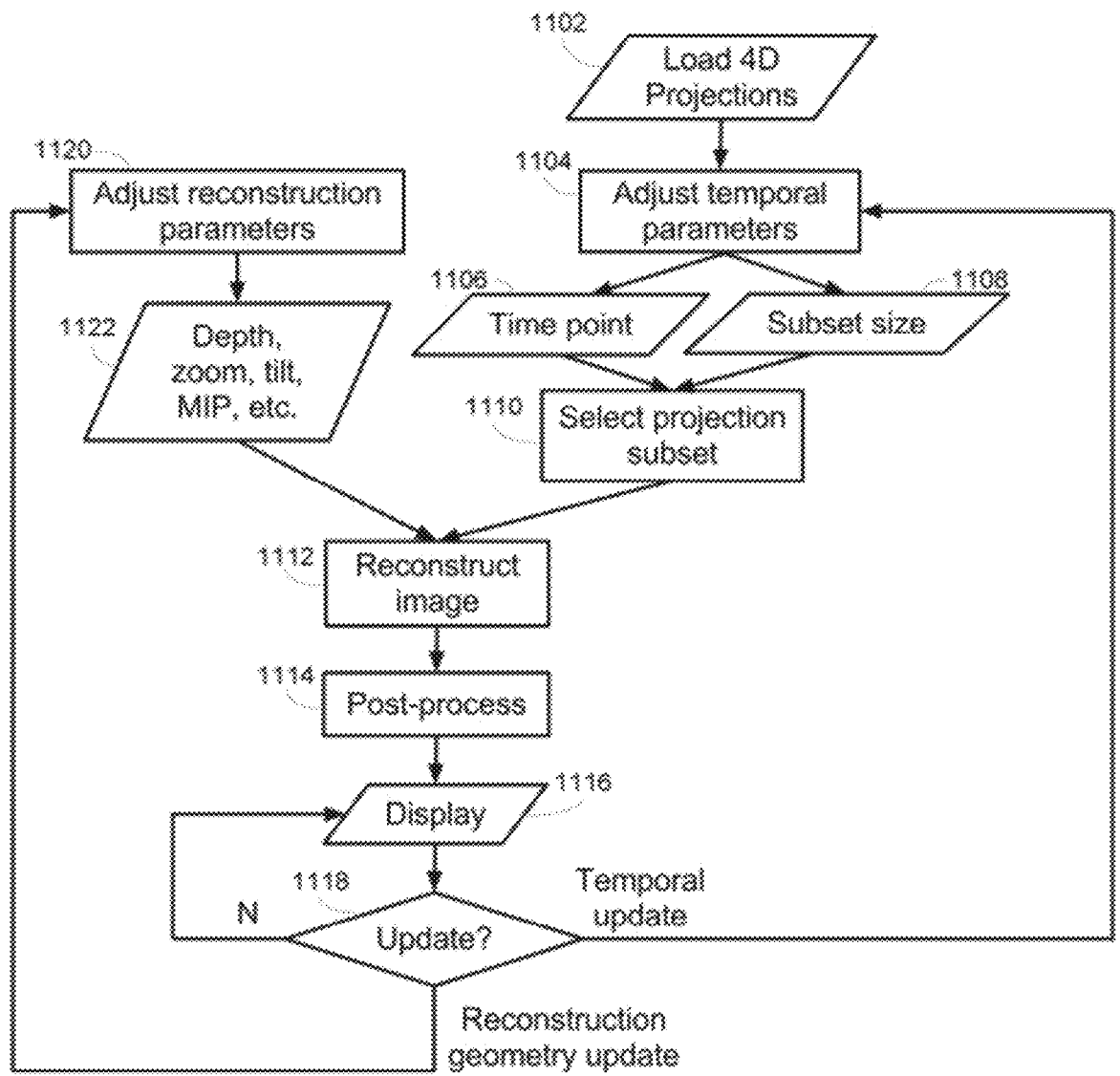
FIG. 11 illustrates a flowchart showing a sample process for providing a four-dimensional tomographic display.

FIG. 11 illustrates a flowchart showing a sample process for providing a four-dimensional tomographic display. A processing device may load 1102 a set of 4D projections, and adjust 1104 any temporal parameters. For example, the processing device may adjust 1104 a time point 1106 and a subset size 1108 for the 4D images as described above. Based upon the adjusted 1104 parameters, the processing device may select 1110 a projection subset. The processing device may reconstruct 1112 the image, perform 1114 any post-processing, and display 1116 the image.

The processing device may determine 1118 if there are any updates to the projections. If there are no updates, the processing device may continue to display 1116 the image. If the processing device determines 1118 there is a temporal update, the processing device may adjust 1104 the temporal parameters, and the process may proceed as before. Alternatively, if the processing device determines 1118 there is a reconstruction geometry update, the processing device may adjust 1120 the reconstruction parameters 1122. The reconstruction parameters 1122 may include, but are not limited to, depth, zoom, tilt, MIP, and other similar parameters. The processing device may then reconstruct 1112 the image and the process proceeds as before.

Another potential enhancement, as listed above, is providing a hybrid dynamic reconstruction. Fully dynamic reconstruction and rendering offers the maximum flexibility for 3D visualization of tomosynthesis data. However, a fully dynamic reconstruction may not be appropriate in all cases. For examples, if GPU resources are limited, or where high resolution datasets with complex geometries need to be visualized with high frame rates, it may be more appropriate to use a hybrid dynamic reconstruction. In a hybrid dynamic reconstruction, a cached stack of pre-reconstructed static slices are initially displayed, and the dynamic reconstruction is only engaged when the user desires views outside of the pre-reconstructed stack. Views which would trigger the dynamic reconstruction could include tilted planes, planes sampled at finer z-depths than the standard slice spacing, a magnified super-resolution region of interest, and other similar views.

Figure 12:
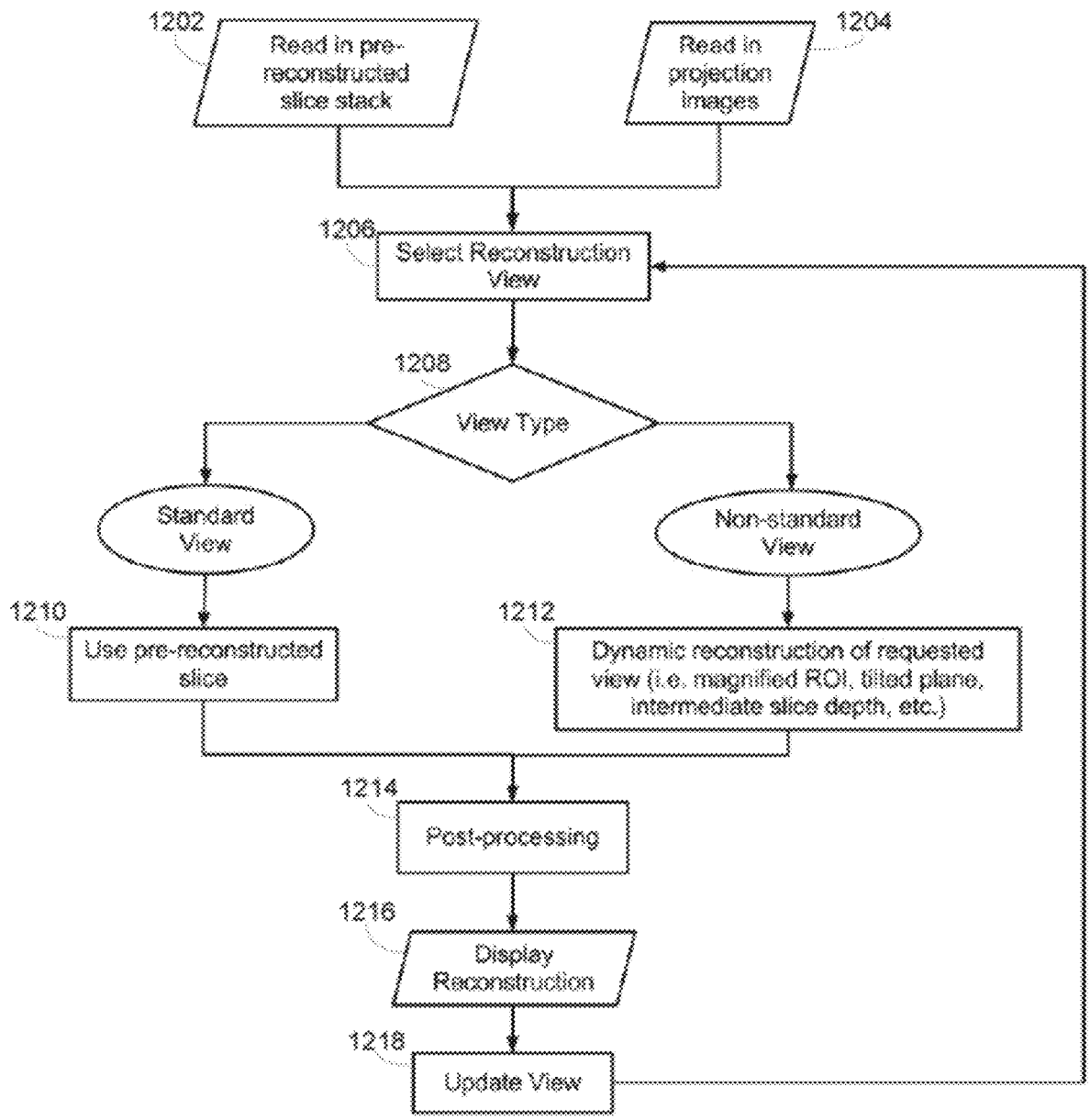
FIG. 12 illustrates a flowchart showing a sample process of hybrid dynamic reconstruction.

FIG. 12 illustrates a flowchart showing a sample process of hybrid dynamic reconstruction. A processing device may load 1202 a pre-reconstructed slice stack of tomographic images, and also load 1204 a set of projection images. The processing device may receive a user selection 1206 to reconstruct a view of an imaged volume. The processing device may determine 1208 what type of view the user has selected 1206, a standard view or a non-standard view.

If the user selected 1206 a standard view, the processing device may use 1210 a pre-reconstructed slice from the loaded set, perform 1214 any post processing, display 1216 the reconstruction and update 1218 the view.

However, if the user selected 1206 a non-standard view, the processing device may perform 1212 a dynamic reconstruction of the requested non-standard view (e.g., a magnified ROI, a tilted plane, an intermediate slice depth, or any other view that cannot be retrieved from the pre-reconstructed slice stack). As with the standard view, the processing device may perform 1214 any post processing, display 1216 the reconstruction and update 1218 the view.

Another potential enhancement, as listed above, is to provide non-planar reconstruction. A typical reconstructed image is of a planar cross-sectional slice through the imaged volume. However, this is not a mathematical necessity for the reconstruction. For any 3D position within the imaged volume, a target at that 3D position will have a focused backprojection, and targets not at that 3D position will have a blurred backprojection. Although they are non-conventional, non-planar reconstructions are valid.

Many anatomical structures have 3D spatial distributions that cannot be fully visualized by a planar cross-sectional reconstruction. For example, blood vessels have complex 3D spatial distributions. Non-planar reconstruction may offer superior visualization of complex 3D structures. One possible implementation of a non-planar reconstruction would be to generate a surface profile based on a segmented boundary (e.g. segmented breast boundary) or based on grayscale level sets, and reconstruction of the surface profile would give a surface view of the target rather than a cross-sectional slice view. Scaling the surface while advancing the reconstruction image position into the structure of interest may give a visualization effect akin to peeling away layers. Another possibility would be to use local grayscale contrast to generate a non-planar surface which follows a high contrast structure (e.g. contrast-filled vessel) to better visualize the full extent of the structure.

Another potential enhancement, as listed above, is dynamically reconstructing a super-resolution image for a ROI to a screen. To dynamically reconstruct a super-resolution image, according to an embodiment, a processing device may start with a 3D image reconstructed to a default zoom level, typically 1.0, displayed on the screen. A user may use a pointing device to specify a region of interest. This can be done in a number of ways. For example, a user can: (1) draw an area on the displayed image to magnify using a GUI tool; and (2) use one or more predefined outlines (e.g., a rectangle) that the user can move and place over the displayed image. The location and area bounded by the outline as selected by the user may define the area that will be reconstructed, and the size of the area to reconstruct defines the zoom level of the reconstruction. Based upon this information, the processing device may reconstruct the image accordingly.

Another potential enhancement may include a method of dynamically filtering an image that is zoomed with super-resolution. As a displayed image is zoomed in upon with super-resolution, the spatial frequencies contained in the image change. To maintain a consistent image look across different magnifications, the filters should be adjusted to account for the changing spatial frequencies in the zoomed images. For example, the filter of an overlaid magnification glass view can be dynamically recalculated to match the filters used on the underlying base image. Another example is dynamically adjusting filters to maintain a consistent image presentation while the end user is zooming into an image.

The systems and processes as described herein may be implemented on a CPU, GPU, FPGAs or any other graphical device. The systems and processes may be provided along with a standard image reconstruction tool such as an imaging system configured to perform DRR, or as a separate set of tools and additional options that may be incorporated into an imaging system via a series of customer purchases or upgrades. Similarly, a portion of the systems and processes as described herein may be provided with an imaging system, while the remaining systems and processes may be incorporated into an imaging system via a series of customer purchases or upgrades.

Figure 13:
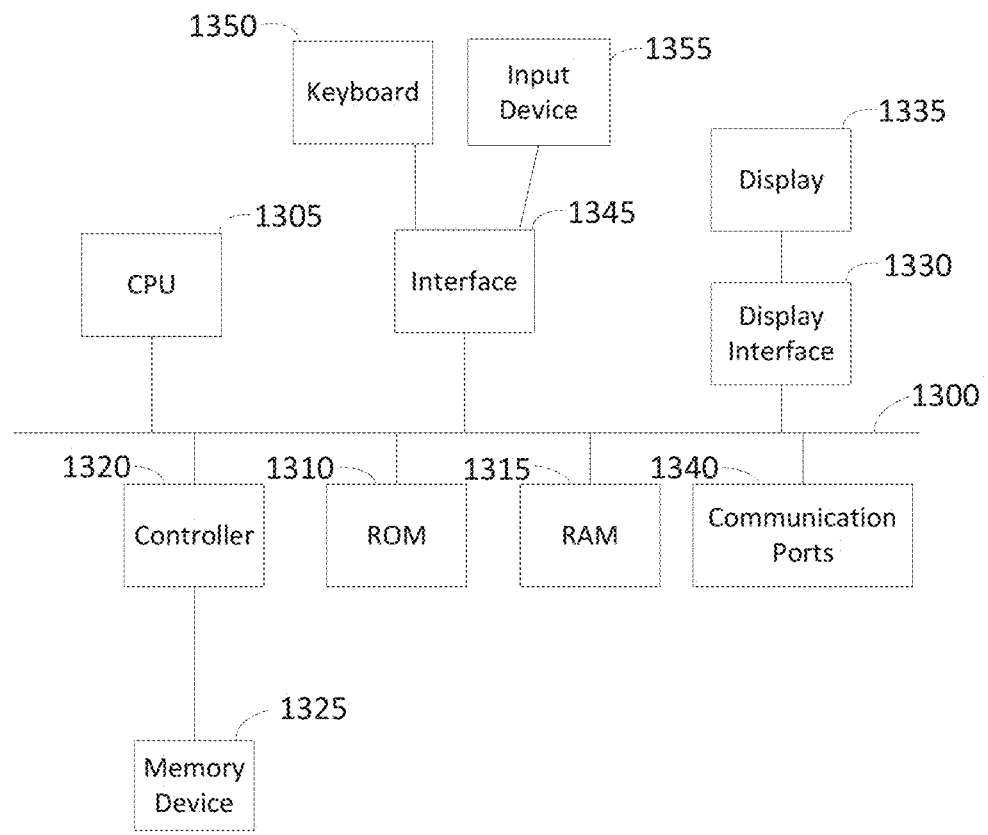
FIG. 13 illustrates various embodiments of a computing device for implementing the various methods and processes described herein.

For example, the systems and processes as described above may be performed and implemented by an operator of a computation workstation include one or more software modules for processing and reconstructing various images. FIG. 13 depicts a block diagram of internal hardware that may be used to contain or implement the various computer processes and systems as discussed above. An electrical bus 1300 serves as the main information highway interconnecting the other illustrated components of the hardware. CPU 1305 is the central processing unit of the system, performing calculations and logic operations required to execute a program. CPU 1305, alone or in conjunction with one or more of the other elements disclosed in FIG. 13, is a processing device, computing device or processor as such terms are used within this disclosure. Additionally, CPU 1305 may be a specialized processing device such as a graphics processing unit. Read only memory (ROM) 1310 and random access memory (RAM) 1315 constitute examples of memory devices.

A controller 1320 interfaces with one or more optional memory devices 1325 to the system bus 1300. These memory devices 1325 may include, for example, an external or internal DVD drive, a CD ROM drive, a hard drive, flash memory, a USB drive or the like. As indicated previously, these various drives and controllers are optional devices. Additionally, the memory devices 1325 may be configured to include individual files for storing any software modules or instructions, auxiliary data, incident data, common files for storing groups of contingency tables and/or regression models, or one or more databases for storing the information as discussed above.

Program instructions, software or interactive modules for performing any of the functional steps associated with the processes as described above may be stored in the ROM 1310 and/or the RAM 1315. Optionally, the program instructions may be stored on a tangible computer readable medium such as a compact disk, a digital disk, flash memory, a memory card, a USB drive, an optical disc storage medium, a distributed computer storage platform such as a cloud-based architecture, and/or other recording medium.

An optional display interface 1330 may permit information from the bus 1300 to be displayed on the display 1335 in audio, visual, graphic or alphanumeric format. Communication with external devices may occur using various communication ports 1340. A communication port 1340 may be attached to a communications network, such as the Internet or a local area network.

The hardware may also include an interface 1345 which allows for receipt of data from input devices such as a keyboard 1350 or other input device 1355 such as a mouse, a joystick, a touch screen, a remote control, a pointing device, a video input device and/or an audio input device.

Several of the features and functions disclosed above may be combined into different systems or applications, or combinations of systems and applications. Various presently unforeseen or unanticipated alternatives, modifications, variations or improvements therein may be subsequently made by those skilled in the art.

The invention claimed is:

1. A method of dynamically reconstructing three dimensional (3D) tomographic images from a set of projection images, the method comprising, by a processing device:
loading a set of projection images into a memory device, wherein the projection images in the set comprise images of a volume acquired at different time points and at different projection angles;
generating a reconstructed 3D tomographic image from the set of projection images to be displayed to a user;
generating a wobble box within which the reconstructed 3D tomographic image can be rotated for a limited range of angles by changing plane orientations of reconstructed slices in the reconstructed 3D tomographic image;
rendering and displaying the reconstructed 3D tomographic image on a display as a four-dimensional tomographic image that incorporates a measurement of time; and
when displaying the reconstructed 3D tomographic image, doing so with the wobble box.

2. The method of claim 1, wherein generating the reconstructed 3D tomographic image from the set of projection images to be displayed to a user comprises:
receiving a time point;
selecting, from the set of projection images, a subset of projection images that were acquired at the time point; and
generating the reconstructed 3D tomographic image from the subset of projection images that were acquired at the time point.

3. The method of claim 1, further comprising:
applying a temporal update to the four-dimensional tomographic image:
selecting, from the set of projection images, a subset of projection images that were acquired an additional time point;
generating a reconstruction geometry for the additional time point from the subset of projection images that were acquired at the additional time point; and
updating the reconstructed 3D tomographic image to display the reconstruction geometry for the additional time point.

4. The method of claim 1, wherein:
generating the reconstructed 3D tomographic image and displaying the reconstructed 3D image as a four-dimensional tomographic image comprises:
identifying, by the processing device, a time point and subset size for the set of projection images;
selecting, by the processing device, a projection set based on the adjusted time point and subset size, and
when generating the reconstructed 3D tomographic image, doing so on the projection set;
the method further comprises, upon receipt of a temporal update:
adjusting the time point for the set of projection images,
selecting, by the processing device, an updated projection set based on the adjusted time point,
using the updated projection set to generate an updated reconstructed 3D tomographic image, and
updating the four-dimensional tomographic image to display the updated reconstructed 3D tomographic image.

5. The method of claim 1, wherein generating the reconstructed 3D tomographic image comprises:
adjusting, by the processing device, a time point and subset size for the set of projection images;
selecting, by the processing device, a projection set based on the adjusted time point and subset size;
when generating the reconstructed 3D tomographic image, doing so on the projection set; and
upon receipt of a non-temporal update to the projection set, adjusting, by the processing device, one or more reconstruction parameters for the projection set and reconstructing the projection images in the projection set accordingly.

6. The method of claim 1 further comprising:
determining a reconstruction method;
wherein generating the reconstructed 3D tomographic image from the set of projection images comprises applying the reconstruction method to the set of projection images.

7. The method of claim 1, wherein the one or more enhancements further comprise providing progressive image load and reconstruction by:
progressively loading the projection images of the data set into a memory; and
before all of the projection images of the set are loaded into the memory:
performing a partial reconstruction using the projection images that have been loaded to yield a partially reconstructed image, causing the display to output the updated partially reconstructed image asynchronously while additional projection images of the set continue to load, and continuing to progressively load the projection images of the set into the memory, perform partial reconstructions, and cause the display to output updated partially reconstructed images until all of the projection images of the set are loaded into the memory.

8. The method of claim 7, further comprising, when all of the projection images in the set are loaded into the memory:
performing a full reconstruction using the projection images of the set to yield the reconstructed 3D tomographic image; and
rendering and causing the display to output the reconstructed 3D tomographic image.

9. The method of claim 1, further comprising:
providing 2D projection image and 3D tomosynthesis image co-registration;
displaying projection and tomosynthesis images that are spatially co-registered in an imaged volume at a same z-depth and orientation.

10. The method of claim 1, further comprising providing dynamic filtering after reconstruction.

11. The method of claim 1, wherein generating the wobble box comprises:
receiving a first location for the wobble box in the reconstructed 3D tomographic image;
defining a region of interest centered at the first location as the wobble box;
generating the reconstructed slices at different locations within the wobble box; and
placing the wobble box at the first location, overlaid on the reconstructed 3D tomographic image.

12. The method of claim 1, wherein generating the reconstructed 3D tomographic image comprises defining an image reconstruction plane comprising three points in an imaged volume by:
receiving, from a user, an indication of the three points on a displayed image volume; and
reconstructing the image volume by aligning a reconstruction plane to a plane defined by the three points as indicated by the user.

13. A non-transitory memory device containing program instructions that are configured to cause a processing device to dynamically reconstruct three dimensional (3D) tomographic images from a set of projection images by:
loading a set of projection images into a memory device, wherein the projection images in the set comprise images of a volume acquired at a different time points and at different projection angles;
generating a reconstructed 3D tomographic image from the set of projection images to be displayed to a user;
generating a wobble box within which the reconstructed 3D tomographic image can be rotated for a limited range of angles by changing plane orientations of reconstructed slices in the reconstructed 3D tomographic image;
rendering and displaying the reconstructed 3D tomographic image on a display as a four-dimensional tomographic image that incorporates a measurement of time; and
when displaying the reconstructed 3D tomographic image, doing so with the wobble box.

14. The memory device of claim 13, wherein the program instructions to generate the reconstructed 3D tomographic image comprise instructions to:
receive a time point;
select, from the set of projection images, a subset of projection images that were acquired at the time point; and
generate the reconstructed 3D tomographic image from the subset of projection images that were acquired at the time point.

15. The memory device of claim 13, further comprising program instructions to:
select, from the set of projection images, a subset of projection images that were acquired an additional time point;
generate a reconstruction geometry for the additional time point from the subset of projection images that were acquired at the additional time point; and
update the four-dimensional tomographic image to display the reconstruction geometry for the additional time point.

16. The memory device of claim 13, wherein:
the program instructions to generate and display the reconstructed 3D tomographic image as the four-dimensional tomographic image comprise instructions to:
identify a time point and subset size for the set of projection images,
select a projection set based on the time point and subset size, and
when reconstructing the 3D tomographic image, do so on the selected projection set; and
upon receipt of a temporal update:
adjust the time point for the set of projection images,
select an updated projection set based on the adjusted time point,
use the updated projection set to generate an updated reconstructed 3D tomographic image, and
update the four-dimensional tomographic image to display the updated reconstructed 3D tomographic image.

17. The memory device of claim 13, wherein the program instructions to generate the reconstructed 3D tomographic image comprise instructions to:
identify a time point and subset size for the set of projection images;
select a projection set based on the time point and subset size;
when reconstructing the 3D tomographic image, do so on the projection set; and
upon receipt of a non-temporal update to the projection set, adjust one or more reconstruction parameters for the projection set and reconstruct the projection images in the projection set accordingly.

18. The memory device of claim 13, further comprising program instructions to provide dynamic filtering after reconstruction.

19. The memory device of claim 13, wherein the program instructions to generate the wobble box comprise instructions to:
receive a first location for the wobble box in the reconstructed 3D tomographic image;
define a region of interest centered at the first location as the wobble box;
generate the reconstructed slices at different locations within the wobble box; and
place the wobble box at the first location, overlaid on the reconstructed 3D tomographic image.

20. The memory device of claim 13, wherein the program instructions to generate the reconstructed 3D tomographic image comprise instructions to define an image reconstruction plane comprising three points in an imaged volume by:
upon receipt, from a user, an indication of the three points on a displayed image volume, reconstructing the image volume by aligning a reconstruction plane to a plane defined by the three points as indicated by the user.

21. A method of dynamically reconstructing three dimensional (3D) tomographic images from a set of projection images, the method comprising, by a processing device:
loading a set of projection images into a memory device, wherein the projection images in the set comprise images of a volume acquired at different time points and at different projection angles;
generating a reconstructed 3D tomographic image from the set of projection images to be displayed to a user;
generating a wobble box within which the reconstructed 3D tomographic image can be rotated for a limited range of angles by changing plane orientations of reconstructed slices in the reconstructed 3D tomographic image; and
rendering and displaying the reconstructed 3D tomographic image on a display with the wobble box.

22. The method of claim 21, wherein generating the reconstructed 3D tomographic image from the set of projection images to be displayed to a user comprises:
receiving a time point;
selecting, from the set of projection images, a subset of projection images that were acquired at the time point; and
generating the reconstructed 3D tomographic image from the subset of projection images that were acquired at the time point.

23. The method of claim 21, wherein generating the reconstructed 3D tomographic image comprises:
adjusting, by the processing device, a time point and subset size for the set of projection images;
selecting, by the processing device, a projection set based on the adjusted time point and subset size;
when generating the reconstructed 3D tomographic image, doing so on the projection set; and
upon receipt of a non-temporal update to the projection set, adjusting, by the processing device, one or more reconstruction parameters for the projection set and reconstructing the projection images in the projection set accordingly.

24. The method of claim 21, further comprising:
determining a reconstruction method;
wherein generating the reconstructed 3D tomographic image from the set of projection images comprises applying the reconstruction method to the set of projection images.

25. The method of claim 21, wherein the one or more enhancements further comprise providing progressive image load and reconstruction by:
progressively loading the projection images of the data set into a memory; and
before all of the projection images of the set are loaded into the memory:
performing a partial reconstruction using the projection images that have been loaded to yield a partially reconstructed image,
causing the display to output the updated partially reconstructed image asynchronously while additional projection images of the set continue to load, and
continuing to progressively load the projection images of the set into the memory, perform partial reconstructions, and cause the display to output updated partially reconstructed images until all of the projection images of the set are loaded into the memory.

26. The method of claim 25, further comprising, when all of the projection images in the set are loaded into the memory:
performing a full reconstruction using the projection images of the set to yield the reconstructed 3D tomographic image; and
rendering and causing the display to output the reconstructed 3D tomographic image.

27. The method of claim 21, further comprising:
providing 2D projection image and 3D tomosynthesis image co-registration;
displaying projection and tomosynthesis images that are spatially co-registered in an imaged volume at a same z-depth and orientation.

28. The method of claim 21, further comprising providing dynamic filtering after reconstruction.

29. The method of claim 21, wherein generating the wobble box comprises:
receiving a first location for the wobble box in the reconstructed 3D tomographic image;
defining a region of interest centered at the first location as the wobble box;
generating the reconstructed slices at different locations within the wobble box; and
placing the wobble box at the first location, overlaid on the reconstructed 3D tomographic image.

30. The method of claim 21, wherein generating the reconstructed 3D tomographic image comprises defining an image reconstruction plane comprising three points in an imaged volume by:
receiving, from a user, an indication of the three points on a displayed image volume; and
reconstructing the image volume by aligning a reconstruction plane to a plane defined by the three points as indicated by the user.

31. A non-transitory memory device containing program instructions that are configured to cause a processing device to dynamically reconstruct three dimensional (3D) tomographic images from a set of projection images by:
loading a set of projection images into a memory device, wherein the projection images in the set comprise images of a volume acquired at a different time points and at different projection angles;
generating a reconstructed 3D tomographic image from the set of projection images to be displayed to a user;
generating a wobble box within which the reconstructed 3D tomographic image can be rotated for a limited range of angles by changing plane orientations of reconstructed slices in the reconstructed 3D tomographic image; and
rendering and displaying the reconstructed 3D tomographic image on a display with the wobble box.

32. The memory device of claim 31, wherein the program instructions to generate the reconstructed 3D tomographic image comprise instructions to:
receive a time point;
select, from the set of projection images, a subset of projection images that were acquired at the time point; and
generate the reconstructed 3D tomographic image from the subset of projection images that were acquired at the time point.

33. The memory device of claim 31, wherein the program instructions to generate the reconstructed 3D tomographic image comprise instructions to:
- identify a time point and subset size for the set of projection images;
- select a projection set based on the time point and subset size;
- when reconstructing the 3D tomographic image, do so on the projection set; and
- upon receipt of a non-temporal update to the projection set, adjust one or more reconstruction parameters for the projection set and reconstruct the projection images in the projection set accordingly.

34. The memory device of claim 31, further comprising program instructions to provide dynamic filtering after reconstruction.

35. The memory device of claim 31, wherein the program instructions to generate the wobble box comprise instructions to:
- receive a first location for the wobble box in the reconstructed 3D tomographic image;
- define a region of interest centered at the first location as the wobble box;
- generate the reconstructed slices at different locations within the wobble box; and
- place the wobble box at the first location, overlaid on the reconstructed 3D tomographic image.

36. The memory device of claim 31, wherein the program instructions to generate the reconstructed 3D tomographic image comprise instructions to define an image reconstruction plane comprising three points in an imaged volume by:
- upon receipt, from a user, an indication of the three points on a displayed image volume, reconstructing the image volume by aligning a reconstruction plane to a plane defined by the three points as indicated by the user.

* * * * *